(12) United States Patent
Frigg

(10) Patent No.: US 6,325,802 B1
(45) Date of Patent: Dec. 4, 2001

(54) SPINAL FIXATION ELEMENT

(75) Inventor: Robert Frigg, Davos-Platz (CH)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 08/325,629

(22) Filed: Oct. 19, 1994

Related U.S. Application Data

(63) Continuation of application No. 08/102,194, filed on Aug. 5, 1993, now abandoned.

(30) Foreign Application Priority Data

Aug. 12, 1992 (CH) .................................................. 2522/92

(51) Int. Cl.$^7$ ..................................................... A61B 17/70
(52) U.S. Cl. ............................................... 606/61; 606/73
(58) Field of Search ................................ 606/53, 54, 59, 606/60, 61, 72, 73

(56) References Cited

U.S. PATENT DOCUMENTS

| | | | |
|---|---|---|---|
| 4,119,091 | * 10/1978 | Partridge | 606/74 |
| 4,569,338 | * 2/1986 | Edwards | 606/61 |
| 4,805,602 | 2/1989 | Puno et al. . | |
| 5,108,399 | * 4/1992 | Eitenmuller et al. | 606/73 |
| 5,190,545 | * 3/1993 | Corsi et al. | 606/60 |
| 5,242,446 | * 9/1993 | Steffee et al. | 606/60 |

FOREIGN PATENT DOCUMENTS

| | | |
|---|---|---|
| 4021246 | 1/1992 | (DE) . |
| 4102462 | 7/1992 | (DE) . |
| 2309198 | 11/1976 | (FR) . |
| WO9203100 | 3/1992 | (WO) . |

* cited by examiner

Primary Examiner—David O. Reip
(74) Attorney, Agent, or Firm—Pennie & Edmonds LLP

(57) ABSTRACT

Spinal column fixation device, in the form of a pedicle screw, has an anchoring section meant for fixation into a bone, and an adjoining head section for attachment to a longitudinal support piece. The head section has an opening that runs all the way through the part, transverse to the plane of symmetry of the fixation device, for the purpose of admitting a tension-stable fastening device which can be looped around longitudinal support piece.

5 Claims, 6 Drawing Sheets

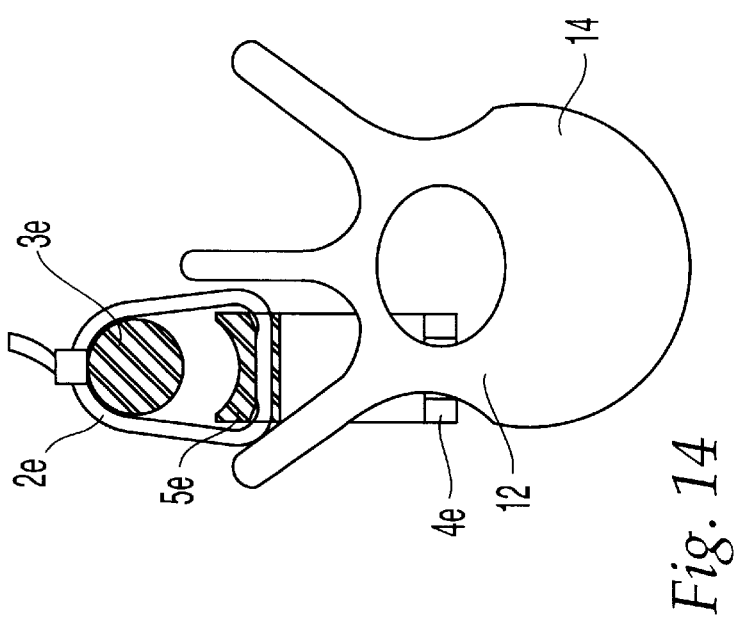
Fig. 12
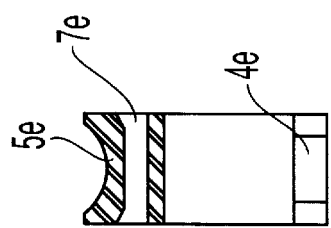
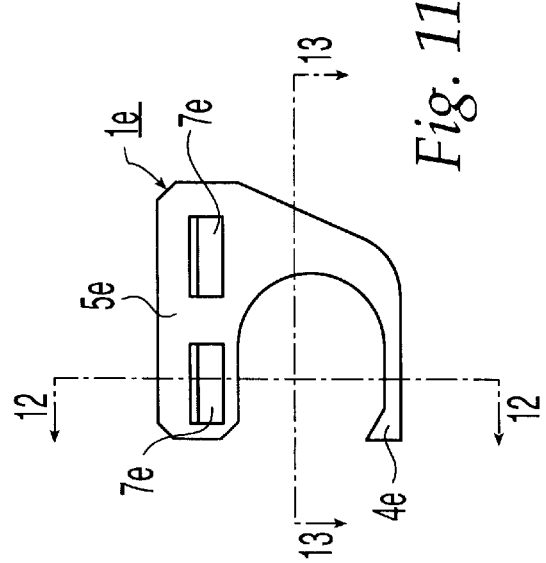
Fig. 11
Fig. 13
Fig. 14

SPINAL FIXATION ELEMENT

This is a continuation of application(s) Ser. No. 08/102,194 filed on Aug. 5, 1993 now abandoned.

FIELD OF THE INVENTION

This invention relates to a spinal column fixation device, in particular a pedicle screw or pedicle hook adapted to be connected to a longitudinal support rod.

BACKGROUND OF THE INVENTION

For posterior spinal column correction, there are fundamentally two types of fixation or anchoring devices, pedicle screws and spinal column hooks. As their name implies, pedicle screws are inserted into the pedicle of the spinal column. Pedicle hooks can be attached either to the pedicle or to the lamina of the spinal body. They are placed primarily in the thoracic area of the spine. For the most part, screws, which are inserted into the spinal body, are used in anterior spinal column correction.

Spinal column fixation devices of this type in the form of a pedicle screw are described, for example, in WO 92/03100.

The problem with all previously known spinal column systems for treatment of spinal column deformities, is that their application is complex. This problem shows up primarily when the individual spinal column fixation devices must be linked with a longitudinal support piece. In contrast to treatment of spinal column fractures, in treating deformities, several of the anchoring devices must be attached to the spinal column. Since the spinal column is deformed, only in very rare cases is it possible to place these anchoring devices in a line. From this comes the problem of connection to a longitudinal support piece which normally consists of a round rod.

In the so-called derotation technique, the longitudinal support piece is pre-bent, and after attachment to the anchoring devices, turned 90 degrees. This results in transformation of a lateral bending of the spinal column into a bending in the sagittal plane. In spite of the initial enthusiasm for this technique, it has been determined that the long term result is only a slight correction.

A correction of the spinal column which is optimal according to current state of the art can be achieved with the so-called frame technique. In this technique, the portion of the spinal column that is to be corrected is bridged by two longitudinal support pieces. Both longitudinal support pieces are attached to the spinal body adjacent to the deformation. In accord with the type of correction desired, the two longitudinal support pieces can be pre-bent. Into the spinal bodies which are bridged by the two longitudinal support pieces, anchoring devices (pedicle screws or pedicle hooks) are attached. With the help of these devices, the individual spinal bodies can now be pulled toward the longitudinal support pieces and attached.

In spite of its advantages relative to all previously known methods, this technique can very seldom be used, because the anchoring devices do not possess sufficient adaptability. In addition to the axial loading, which is desired, they cause unnecessary bending loads, since they must be rigidly linked to the longitudinal support piece. These additional loads are so great that at older defective locations in the spinal column, they can lead to a tearing out of the anchoring devices. This tearing-out problem occurs very frequently, since attachment of the anchoring device to the longitudinal rod can be done only in one position. That is, if the correction of the spinal column by its ossification is not 100% feasible, then this partially completed correction cannot be kept in this position. For this reason, often too much force is applied to achieve 100%, and indeed not because of the correction, but rather because of the required attachment of the anchoring devices to the longitudinal support piece. The only alternative is the intermediate insertion of a third longitudinal support piece, which must be attached to an existing longitudinal support piece via a connecting piece. This quantity of implants, however, often exceeds the biological tolerance limit and impairs the functioning of the spinal column musculature.

Presently known individual attachment devices (for example, in accord with WO 92/03100) have an improved adaptation, but are at the tolerance limit especially in young patients, because of their size. A large size proves to be negative above all in complex corrections, since almost every spinal column which is equipped with such an implant, and the spinal column musculature, suffers from it.

SUMMARY OF THE INVENTION

The present invention affords a remedy for this problem by providing a spinal column fixation device which permits optimal choices to correct the spinal column, while at the same time reducing the bulk of the implant to a minimum.

The invention provides a spinal column fixation device such as a pedicle screw or hook comprising an anchoring element for fixation to the bone, and a head section connected to the anchoring element, said head section comprising a transverse opening shaped to receive a tension stable fastening element for attachment to a longitudinal support piece.

The invention also provides a spinal column fixation assembly comprising a fixation device as described, a longitudinal support piece and a tension stable fastening element shaped to extend through the transverse opening in the head section and connect the device to the support piece.

BRIEF DESCRIPTION OF THE DRAWINGS

The invention will be further described with reference to the drawings in which:

FIG. 11 is a side elevational view of a spinal column fixation device according to the invention in the form of a spinal column hook.

FIG. 12 is a front elevational view partly in vertical section of the device of FIG. 11, the section being taken on the line 12—12 of FIG. 11.

FIG. 13 is a horizontal section through the spinal column hook of FIG. 11, along the line 13—13.

FIG. 14 shows schematically the spinal column hook of FIGS. 11–13 attached to the bone which is pulled toward a longitudinal support piece by a fastening device.

DETAILED DESCRIPTION OF THE INVENTION

Figure 2:
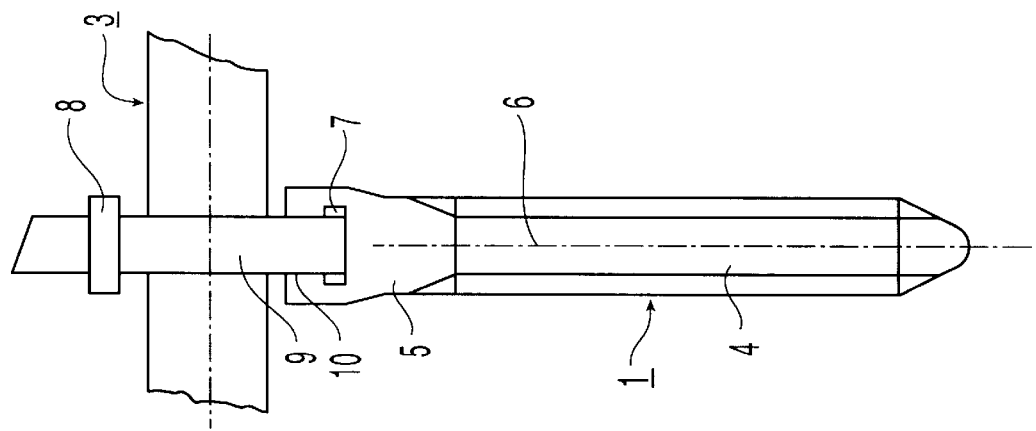
FIG. 2 is a view in side elevation showing the device of FIG. 1.
Figure 1:
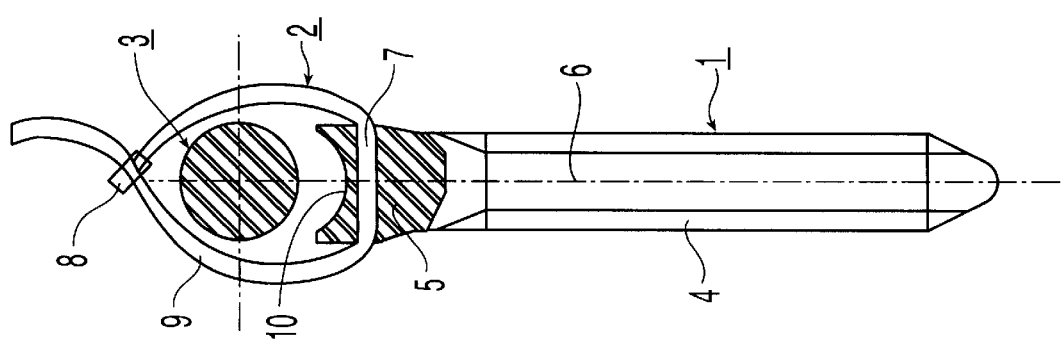
FIG. 1 is a view in front elevation and partially in vertical section of a spinal column fixation device according to the invention in the form of a pedicle screw, in a position to be attached to a longitudinal support piece by means of a fastening device.
Figure 4:
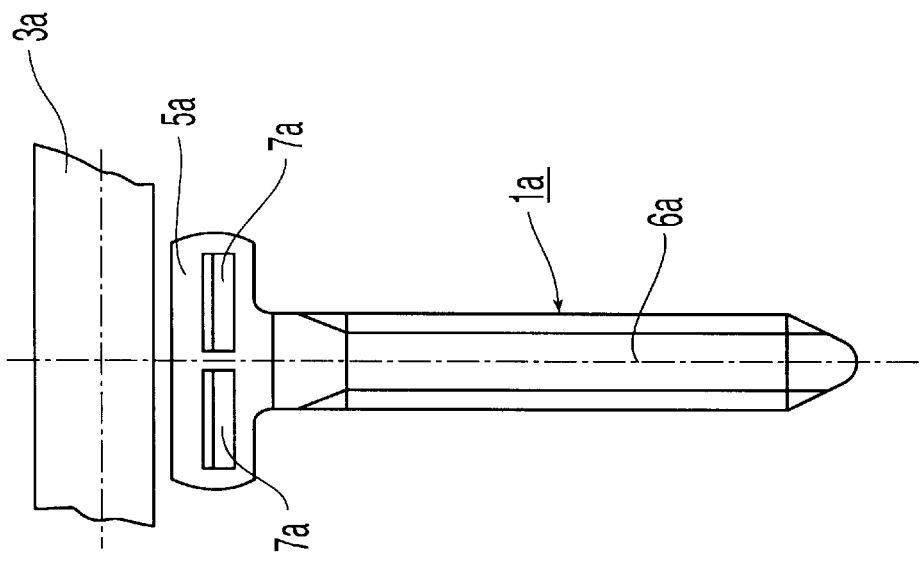
FIGS. 3 and 4 are front and side elevational views, partly in vertical section, of a spinal column fixation device according to the invention with a double slot.

Referring to FIGS. 1 and 2, a spinal column fixation assembly according to the invention comprises a spinal column fixation device 1, a tension-stable fastening element 2 and a longitudinal support piece 3. The spinal column fixation device 1 comprises an anchoring element 4 for fixing into the bone (here in the form of a screw), and a head section 5 connected to the anchoring element, which head section is meant for attachment to longitudinal support piece 3. The head section exhibits an opening 7 running all the way through it, and transverse to the plane of symmetry 6 of the fixation device, to admit the fastening element 2 which can be looped around longitudinal support piece 3.

The tension-stable fastening element 2 for its part consists of a belt-shaped loop 9 closeable by a closing piece 8 and movable only in one direction, i.e. in a direction to make it smaller. By tightening loop 9, it is possible to draw spinal column fixation device 1 closer to longitudinal support piece 3, and optimally to bring it so that it is contiguous with it. For this purpose, the head section 5, on its end intended to be adjacent to longitudinal support piece 3, is equipped with a concave surface 10, which matches the convex surface of the longitudinal support piece 3.

In FIGS. 3—8, various versions of the head section of spinal column fixation devices are depicted.

Figure 3:
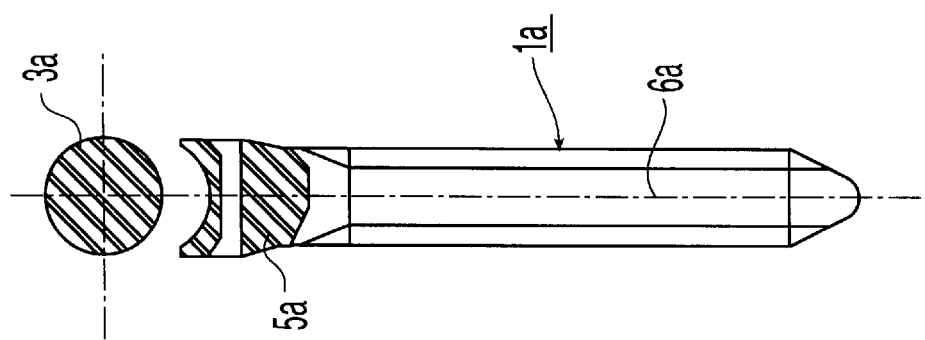
Figure 6:
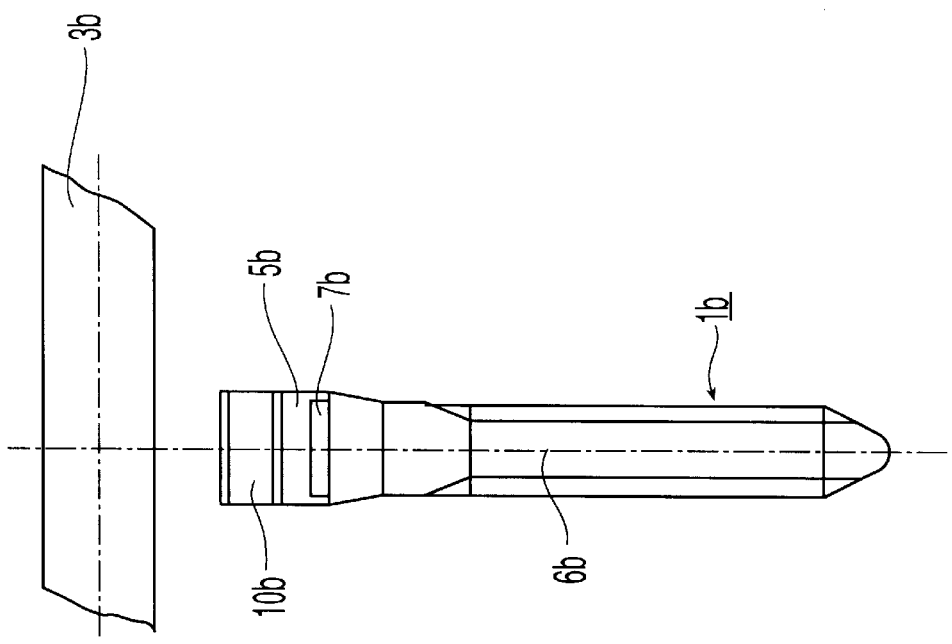
FIG. 6 is a side elevational view of the device of FIG. 5.
Figure 5:
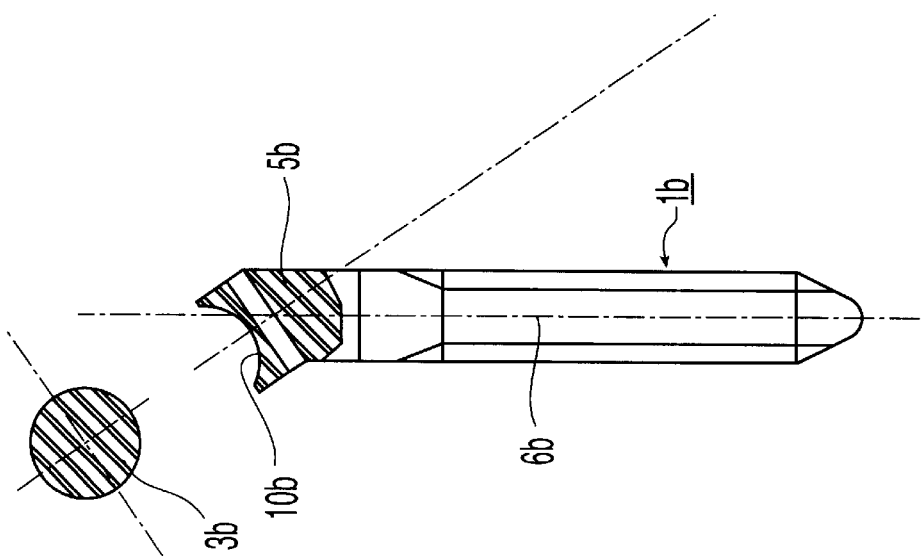
FIG. 5 is a front elevational view, partly in vertical section of a spinal column fixation device according to the invention with a laterally inclined longitudinal groove in the head section.
Figure 8:
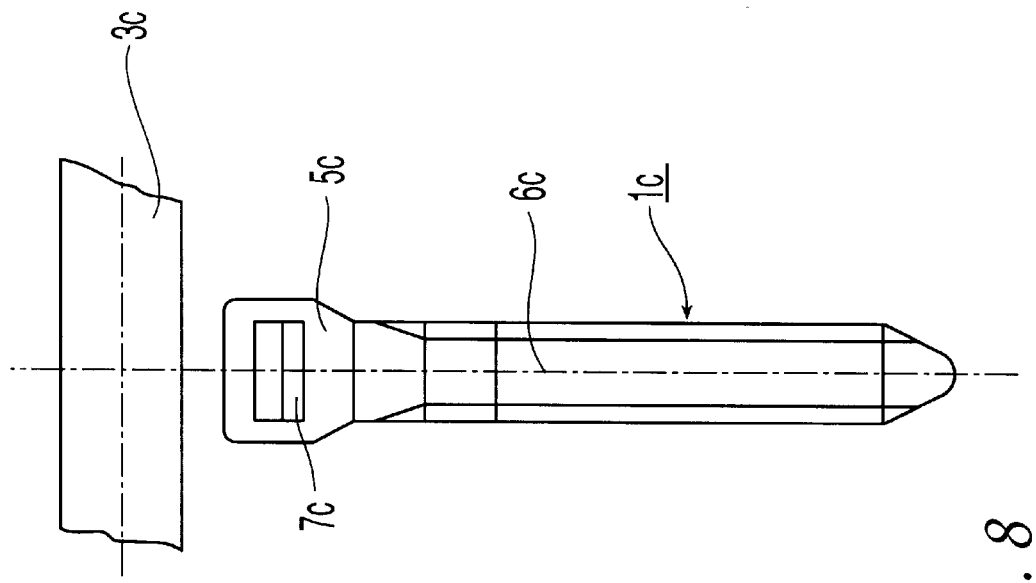
FIG. 8 is a side elevational view of the device of FIG. 7.
Figure 7:
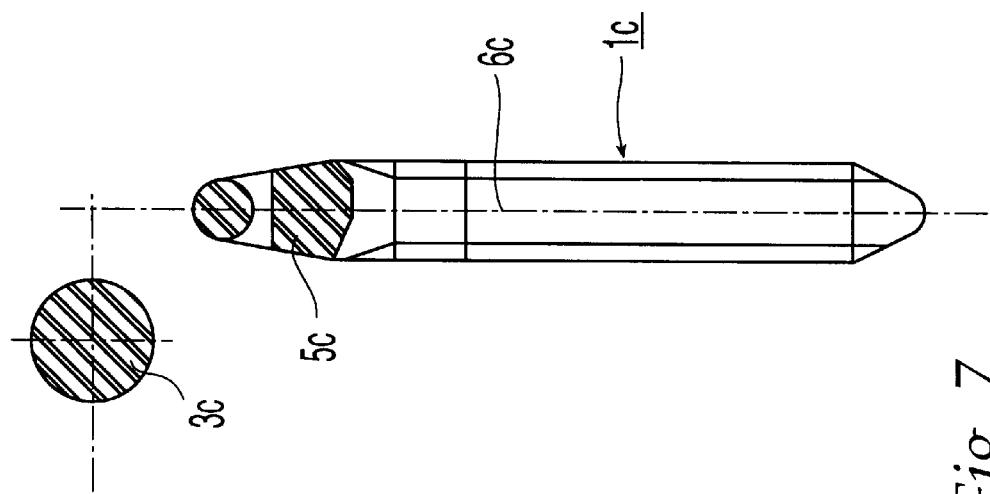
FIG. 7 is a front elevational view partly in vertical section of a spinal column fixation device according to the invention with a miniaturized head section.

In the design configuration according to FIG. 3, head section 5a widens out to admit two separate openings 7a in the form of slots. In the version of FIGS. 5 and 6, head section 5b is tipped down relative to the central axis 6b, in order to bring it laterally closer to longitudinal support piece 3b. Finally, the version of FIGS. 7 and 8 has a head section 5e that has been reduced in order to keep the implant size to a minimum.

Figure 10:
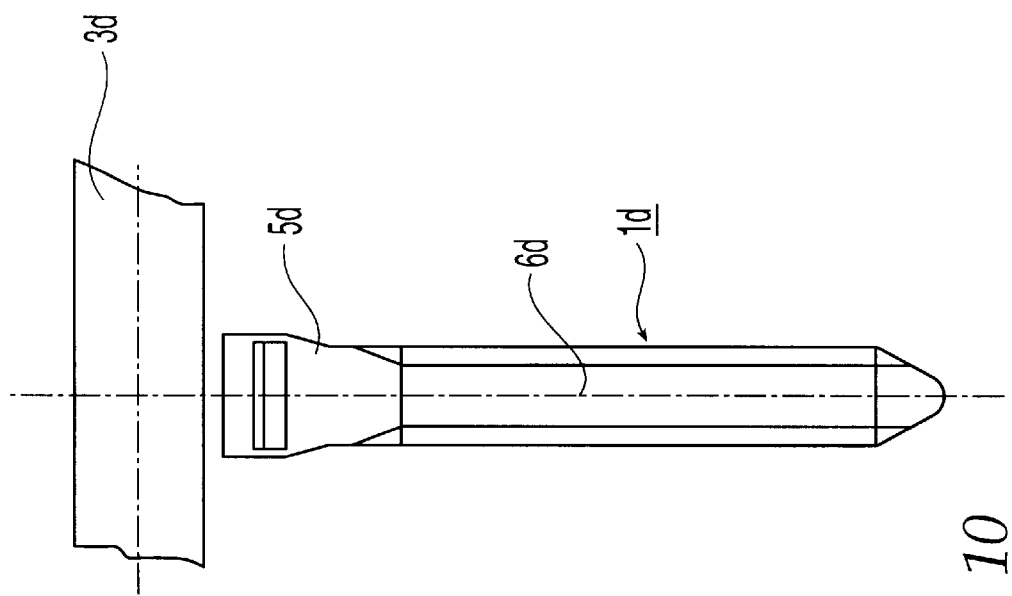
FIG. 10 is a side elevational view of the device of FIG. 9.
Figure 9:
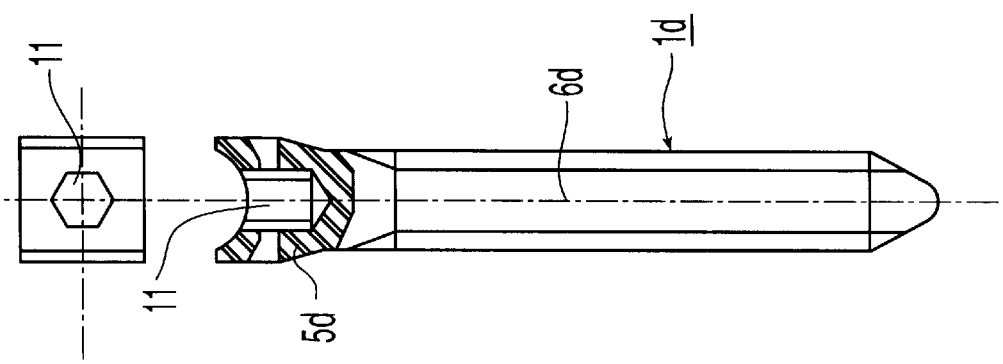
FIG. 9 is a front elevational view partly in vertical section of a spinal column fixation device according to the invention with a central hexagonal socket in the head section.

In FIGS. 9 and 10, a spinal column fixation device 1d is depicted whose head section 5d has a central hexagonal socket 11 running in the direction of the plane of symmetry 6d. This facilitates screwing the pedicle screw into the bone with a suitable hexagonal screwdriver.

In FIGS. 11–14, a spinal column fixation device 1e is depicted in the form of a spinal column hook. This consists of an anchoring element 4e for fixation into the bone, here formed as a two-sided blade, and an adjoining head section 5e for attachment to longitudinal support piece 3e. The head section 5e displays two openings that run clear through the section, and transverse to the plane of symmetry 6e of the spinal column fixation device. These openings are to admit the tension-stable fastening device 2e which can be looped around longitudinal support 3e.

The two-sided blade of the anchoring segment 4e is formed in such a way that it encloses the pedicle 12 of spinal body 14.

From the foregoing it can be seen that a fundamental of the fixation device according to the invention is in the way in which the individual spinal column fixation devices are coupled to a longitudinal support piece. In place of the previously used connections (which were rigid in all directions) between the fixation device and the longitudinal support piece, the connection according to the invention is fixed only in the axial tension direction. That means that each individual spinal body is drawn toward the longitudinal support piece by tension. It does not matter whether 100% correction can be achieved or not. Through the attachment, stable in the axial direction, of the attachment devices to the longitudinal support piece, the spinal column is maintained in the corrected position. The force that acts on the spinal body during correction is like the action of a rope on the spinal body. This has the additional advantage that during the course of correction, the spinal body can seek its "path" on its own. Most of all this has advantages in correcting long-term deformed spinal columns, since during the deformity which has continued over a long period the spinal elements have become deformed themselves and can become interlocked into each other.

Forces which act axially on the spinal column are not transferred to the spinal column fixation devices, but rather are carried by the spinal bodies. If this is not desired, the axial forces as well as the torsional forces can be transferred by a frame structure such as that referred to above. This frame structure consists of conventional anchoring devices which are rigid in all directions; they are attached to one or two longitudinal support pieces. Attachment of this frame is not a problem, since in each case only two rigid fixation devices are connected to each other. By displacement of the proximal fixation devices to the distally attached fixation devices, the spinal column area within the frame can be relieved of loading. Torsional and axial loadings are carried totally by the frame. An elastic fixation of the spinal column, which has a healing influence on the spinal column, can be achieved by long-extension bridging.

At the same time, the longitudinal support piece will protect the bone anchoring device interface (pedicle screw or spinal column hook) from being subjected to excessive loads. The fixation devices of the invention will then be used within the frame, to effect the actual correction. The correction of the individual spinal bodies can be done by degrees. In other words, each spinal element will alternate in being drawn to the longitudinal support piece in incremental fashion. This procedure will avoid an overloading of the implant anchoring into the bone.

In addition to its improved functioning, the spinal column fixation device according to the invention also is distinguished by being very simple to use.

As brought out above fixation devices according to the invention may have either one or two slots on their head sections, through each of which an attachment device known in the technology as a cable binder is passed. As described above, such tension-stable fastening devices consist essentially of a closed loop which moves via a locking piece in only one direction, i.e. it can be reduced in size. Examples of such fastening devices are described in detail in the German published patent applications DE-A1 40 24 334 and DE-A1 40 21 246, where direct application is made to bones, and not as a connecting piece between two osteosynthetic structural elements.

As described above the head of the pedicle screw and pedicle hook according to the invention can be configured in various ways. If it has been determined, with the aid of X-ray imaging, that a 100% correction can be achieved, then screws and/or hooks can be employed which possess a longitudinal groove on the head end that matches the longitudinal support piece. After correction has been carried out, the fastening devices in these pieces can be replaced by metal clasps. These metal clasps have an advantage in that they can, if necessary, accept forces in all directions. Thus, in simple spinal corrections, a frame can be dispensed with if the need arises.

In another variant of the invention, the head of the fixation device is shaped so that the groove matches the longitudinal support piece placed laterally in the implant head. This head shape can be used where the longitudinal support piece comes to lie laterally with respect to the anchoring device in its final position. Once again, X-ray imaging can be employed beforehand to establish the final positions of the longitudinal support piece and the anchoring device. As described a third head shape is configured in such a way that it has the smallest possible dimensions, and possesses only the slot for receiving the fastening device. This anchoring device generally is used where small implant size is a priority, or where 100% correction cannot be achieved.

In another form, described above in connection with FIGS. 11–14, the spinal column fixation device, particularly where it is designed as a spinal column hook, has a double slot. Each slot, made on the head end, has different requirements. The slot placed before the tip of the hook serves to admit a correction fastening device. When this correction fastening device exerts axial forces on the hook, the latter has a tendency to tip downward, which causes it to hook more effectively into the spinal body. The second slot serves to admit the fixation fastening device. This slot is located in the extension of the hook base. After correction has been carried out, a fastening device is placed through this slot to achieve improved stability of the hook.

Depending on the application, the spinal column fixation devices as well as the longitudinal support pieces can be fabricated from implant steel, titanium, titanium alloys, plastics or biodegradable materials. The same is true for the fastening devices. The fixation assembly as a whole might be made of non-resorbable plastic and the fastening element of resorbable or non-resorbable plastic. One preferred combination of materials consists of titanium for the spinal column fixation device and the longitudinal support pieces, and plastic for the fastening devices. This combination of materials has an advantage in that with modern options for follow-up testing (MRI, CAT, etc.), it does not have negative effects.

It is claimed:

1. A spinal column fixation assembly comprising a longitudinal support piece having a longitudinal axis, a fixation device having an anchoring element with a major axis for fixation to a bone and a head section formed as a single piece with said anchoring element, said head section having a channel for receiving said support piece and a slot extending through said fixation device along an axis transverse to the axis of a support piece positioned in said channel and intersecting the major axis of the anchoring element, said assembly further comprising a tension stable fastening element extending through said slot and around said support piece to secure said support piece in said channel.

2. The fixation assembly claimed in claim 1, wherein the anchoring element, the head section, and the longitudinal support piece are titanium and the fastening element is resorbable plastic.

3. The fixation assembly of claim 1, wherein the assembly consists in its entirety of titanium or a titanium alloy.

4. The fixation assembly of claim 1, wherein the assembly consists in its entirety of non resorbable plastic.

5. The fixation assembly of claim 1, wherein said fastening element comprises a belt formed in a loop and a closure element in said belt and moveable along said belt in one direction only.

* * * * *